United States Patent
Borggaard et al.

(10) Patent No.: US 6,649,412 B1
(45) Date of Patent: Nov. 18, 2003

(54) METHOD AND APPARATUS FOR DETERMINING QUALITY PROPERTIES OF FISH

(75) Inventors: Claus Borggaard, Viby Sjælland (DK); Lars Bager Christensen, Gadstrup (DK); Knut Erik Gulbrandsen, Nesttun (NO); Allan J. Rasmussen, Fuglebjerg (DK)

(73) Assignee: Marine Harvest Norway AS (NO)

( * ) Notice: Subject to any disclaimer, the term of this patent is extended or adjusted under 35 U.S.C. 154(b) by 0 days.

(21) Appl. No.: 10/048,100

(22) PCT Filed: Jul. 19, 2000

(86) PCT No.: PCT/DK00/00411
§ 371 (c)(1),
(2), (4) Date: May 3, 2002

(87) PCT Pub. No.: WO01/09587
PCT Pub. Date: Feb. 8, 2001

(30) Foreign Application Priority Data

Jul. 28, 1999 (DK) .......................... 1999 01070

(51) Int. Cl.[7] .............................................. G01N 21/25
(52) U.S. Cl. ........................... 436/20; 436/20; 436/60; 436/164; 422/82.09
(58) Field of Search .............................. 436/20, 21, 60, 436/71, 164; 42/82.05, 82.09; 250/339.11, 341.8; 356/445, 406, 425, 402

(56) References Cited

U.S. PATENT DOCUMENTS

| | | | |
|---|---|---|---|
| 4,154,864 A | 5/1979 | Risler et al. ............... 426/594 |
| 4,978,225 A | * 12/1990 | Reimer | |
| 5,013,906 A | 5/1991 | Miyakawa et al. | |
| 5,088,822 A | * 2/1992 | Kanda | |
| 5,229,726 A | * 7/1993 | Kent | |
| 5,239,180 A | 8/1993 | Clarke | |
| 5,352,153 A | * 10/1994 | Sengupta et al. | |
| 5,760,406 A | * 6/1998 | Powers | |
| 6,014,222 A | * 1/2000 | Rasmussen et al. | |
| 6,118,542 A | * 9/2000 | Rasmussen et al. | |
| 6,265,882 B1 | * 7/2001 | Nielsen et al. | |
| 6,371,051 B1 | * 4/2002 | Cawthorn et al. | |

FOREIGN PATENT DOCUMENTS

| | | |
|---|---|---|
| EP | 0221642 A2 | 8/1986 |
| EP | 0402877 A1 | 6/1990 |
| WO | 98/49904 | 11/1998 |

* cited by examiner

Primary Examiner—Jeffrey Snay
(74) Attorney, Agent, or Firm—Vidas, Arrett & Steinkraus, P.A.

(57) ABSTRACT

This invention relates to a method and an apparatus for determining quality properties of fish on the basis of light reflection. A fish and a reflection measurement device (5) with a light emitter and a light receiver (6) are positioned in relation to each other, with the light emitter and light receiver of the device directed towards the fish's inner abdominal wall with peritoneum, so that the light emitter illuminates an area of the fish through the peritoneum and the light receiver captures the light reflected from the fish. The intensity of the reflected light is registered in three or more different wavelength bands, in the visible and near-infrared range. Measurement results registered are, after any processing, entered into an algorithm in a calculation unit, where the algorithm expresses a quality property of the fish.

29 Claims, 5 Drawing Sheets

METHOD AND APPARATUS FOR DETERMINING QUALITY PROPERTIES OF FISH

The present application in the U.S. National Stage of PCT Application No. PCT/DK00/00411 filed Jul. 19, 2000, claiming priority to Danish Patent Application Serial No. PA 1999 01070 filed Jul. 28, 1999, the entire contents of which are incorporated herein by reference.

This invention relates to a method and an apparatus for determining quality properties of fish on the basis of light reflection. A fish and a reflection measurement device (5) with a light emitter and a light receiver (6) are positioned in relation to each other, with the light emitter and light receiver of the device directed towards the fish's inner abdominal wall with peritoneum, so that the light emitter illuminates an area of the fish through the peritoneum and the light receiver captures the light reflected from the fish. The intensity of the reflected light as registered in three or more different wavelength bands in the visible and near-infrared range. The measurement results registered are, after any processing, entered into an algorithm in a calculation unit, where the algorithm express a quality property of the fish on the basis of the reflection of its inner abdominal wall with peritoneum and three or more different wavelength bands in the visible and near-infrared range. The calculation unit automatically calculates the quality property by means of the algorithm and measurement results. The intensities of reflected light are registered in both the visible range, especially between 400 nm and 600 nm and in the near-infrared range, especially between 850 nm and 1050 nm. By means of the method it is possible to measure quality properties of individual fish in a short time in a non-destructive manner, especially the color, Astaxanthin content, and/or fat content of Salmon.

The present invention relates to a method and an apparatus for determining quality properties of fish.

Before farmed salmon is slaughtered in a processing factory, a primary check of meat colour is made. For this purpose ten or so fish are taken from each pond and a piece of fillet cut from behind the vent. An operator compares the colour of the cut fillet in an area near the middle of the fish with the colours on a discrete colour chart containing different colour classes. The results of these test samples are assumed to be representative of the whole pond stock.

Both in production and sales, colour is the most important quality parameter for salmon. Salmon buyers can request information on the colour of a delivered lot in the form of a number corresponding to a colour number or a colour step on the Roche scale, a colour table. Another salmon colour reference is the colour number on the Salmo-fan scale.

To meet consumer requirements, farmed salmon production is adjusted to give the finished fish the most sought-after colour. The producer can use the content of astaxanthin in the feed to control the colour, as there is a correlation between the administration of this substance and the meat colour of the slaughtered salmon.

The fat content of salmon is another important quality parameter. Buyers dislike fish with too high a fat content. Chemical analysis of fat content is part of production control, but it too has to be carried out by random sampling.

The means currently available for controlling production and supplying customers with salmon of the desired quality are thus relatively crude and labour-intensive.

In EP 0 221 642 (Westinghouse Canada Inc.) a hand-held apparatus is described for grading fish fillets, i.e. cleaned fish cuts. The apparatus illuminates the fillet and measures the strength of the reflected light at defined wavelengths at which haemoglobin exhibits special absorption properties. The apparatus compares the values at different wavelengths with values in a stored data set and assigns to the fillet the colour class with the best match between the values and the data set. Haemoglobin is undesirable in fish fillets as it may lead to more rapid deterioration of the fillets. A quality measure for whitefish fillets measured with this device is that the meat is white.

The above-mentioned methods for measurement of colour require a cutting of the fish to produce a meat surface which can be used for the measurement. As a consequence, the measurement is either destructive or is performed at a relatively late stage of the slaughter process providing few opportunities for controlling the process according to colour of fish meat. Furthermore, currently used methods for determination of salmon quality can only provide one quality parameter each, necessitating several analysis procedures for determining both colour and fat content.

The purpose of the present invention is to provide an objective method for determining quality properties of fish wherein the above mentioned disadvantages are avoided, enabling the quality properties of individual fish to be measured in a short time in a non-destructive method, in particular a method enabling measurement of colour, astaxanthin content and/or fat content of salmon. It is in particular the purpose of the invention to provide a method for determining quality properties of freshly slaughtered fish on a slaughter line or in a grading machine so that each individual fish can at an early stage of processing be graded as to quality properties and subsequently be processed or sold for further processing in accordance with its properties.

The invention is based on the observation that it is possible to determine quality properties of fish, especially meat colour of salmon, by means of light reflectivity of their inner abdominal wall with peritoneum using wavelength bands in the visible and near-infrared range. This is a surprise because the peritoneum of e.g. salmon is mainly opaque to the eye and prevents a subjective evaluation of the colour of the meat lying behind the peritoneum. The ability of the invention to measure meat colour may to a great extend be based on the fact that measurement is performed also in the near-infrared range and that the reflection data thus abtained are used in the algorithm to calculate the properties.

The method of the invention is characterised in that,
a fish and a reflection measurement device with a light emitter and a light receiver are positioned in relation to each other with the light emitter and light receiver of the device directed towards the fish's inner abdominal wall with peritoneum, so that the light emitter illuminates an area of the fish through the peritoneum and the light receiver captures light reflected from the fish,
the intensity of reflected light is registered in three or more different wavelength bands in the visible and near-infrared range, and
the measurement results registered are, after any processing, entered automatically into an algorithm in a calculation unit, which algorithm expresses a quality property of fish on the basis of the light reflection from the inner abdominal wall with peritoneum, after which the calculation unit automatically calculates the quality property by means of the algorithm and the measurement results.

It is possible to use the method according to the invention for on-line measurement on a slaughter line or in a grading machine for freshly slaughtered fish by using a fully automated equipment and for random sample check at ponds or in processing factories by use of a hand-held instrument.

Advantageous embodiments of the method according to the invention are as follows:

To avoid repeated stoppages on an automated slaughter line or in a grading machine it is an advantage if the measurement can be carried out without interruption, so that the fish continue their movement during the measuring process. One embodiment of the method according to the invention is therefore characterised in that the fish and the light emitter and light receiver of the device are moved in relation to each other in the lengthways direction of the fish during registration of measurement results.

Preferably, a reflection measurement device is used wherein the light receiver is designed to receive light reflected from an area of the fish with a cross dimension of at least 5 mm and at most 25 mm, and the device and the fish is moved in relation to each other so that measurement results are obtained from areas which together form a stripe in the lengthways direction of the fish, with a length of 2.5 to 25 times said cross dimension.

It is an advantage to register several sets of measurement data and especially to register measurement data from different areas of the fish, in order to arrive at a quality property result less affected by noise. Variations in the nature of the meat may thereby be equalized by the calculation of an average and any data for abnormal areas can be eliminated before the property is finally calculated. Preferably, measurement data is registered for different areas of the fish and at least one set of measurement values is used to express the quality property of the fish. Data from different areas may be registered by means of a measurement head which is moved in the lengthways direction of the fish while repeatedly measuring light reflections from new areas of the fish. Another possibility is to use a measuring head with a number of detectors, each covering its own area of the fish. The influence on the measurement of noise and faulty areas can be reduced by the combination or selection of significant measurement values.

Reflection values are preferably registered from different parts of the fish in that the fish is transported past a measurement head and several measurement sequences are recorded, from which one or more may be used in the calculation of the quality property. This simplifies the design of the measurement head. One embodiment is therefore characterised in that the registration is repeated several times, that the fish and the light emitter and light receiver of the device are moved in relation to each other between two measurement sequences, and that at least one set of data resulting from the registrations is entered into the algorithm.

The fish may be cut open in the abdomen and eviscerated before the measurement head of the device and the fish are positioned in relation to each other, by which positioning the measurement head preferably is placed in contact with the peritoneum of the inner abdominal wall of the fish.

Preferably, the intensity of reflected light is registered in the visible and near-infrared range between 400 and 1100 nm. The intensity of reflected light may be registered both in the visible range, preferably between 400 and 600 nm, and in the near-infrared range, preferably between 850 and 1050 nm.

The light emitter may illuminate an area of the fish with broad-spectrum light in the visible and near-infrared range. Division of the reflected light into the different wavelength ranges is then carried out by filtering or spectral dispersion of the light.

The registered measurement results can advantageously be used to determine two or more quality properties, such as colour and fat content. One embodiment of the method according to the invention is therefore characterised in that measurement results registered are entered into an algorithm expressing another quality property of fish, after which the calculation unit automatically calculates this quality property by means of the algorithm and the measurement results. This may be a different algorithm from what is used to determine the first property, but a single algorithm developed to calculate two property values from the same set of measurement data may also be used.

The term "property values" does not necessarily designate a number, such as a step on a colour scale or a percentage fat content. A property or property values may be expressed by a category name, such as dark, normal or light colour, or fatty, normal or lean meat. Combinations of different properties, e.g. colour and fat content, may also express a value. If a buyer has a preference for normally coloured meat containing little fat, the property may simply consist of approval or rejection of the meat for that customer.

In particular it is preferred that quality properties are determined on-line on a slaughter line or in a fish-grading machine and that the fish is conveyed into, through and out of a reflection measurement device mounted on the slaughter line or in the grading machine.

The apparatus according to the invention for determining quality properties of fish is characterised in that it comprises:

a reflection measurement device with a light emitter and a light receiver and arrangements to assist in the positioning of the device and the fish in relation to each other, the light emitter and light receiver of the device being directed towards the inner abdominal wall with peritoneum of the fish, so that the light emitter illuminates an area of the fish through the peritoneum and the light receiver captures light reflected from the fish, registration means connected to the light receiver of the reflection measurement device, which means are designed to register the intensity of reflected light in three or more different wavelength bands in the visible and near-infrared range, and a calculation unit with an algorithm expressing a quality property of a fish from the light reflection of the inner abdominal wall with peritoneum in three or more different wavelength bands in the visible and near-infrared range, the unit being arranged to enter measurement results automatically, after possible processing, into the algorithm and to calculate the quality property automatically by means of the algorithm and the measurement results.

Advantageous embodiments of the device according to the invention are as follows:

The apparatus may comprise a conveyor arranged to move the fish and the light emitter and light receiver of the device in relation to each other in the lengthways direction of the fish during registration of measurement results.

The apparatus may also comprise means for registering the intensity of reflected light in different areas of the fish, In particular, the apparatus may comprise means for repeating the registration several times and a conveyor arranged to move the fish and the light emitter and light receiver of the device in relation to each other between two measuring sequences.

The light emitter may be of such nature that it emits broad-spectrum light in the visible and near-infrared range.

The calculation unit may contain an algorithm expressing another quality property of fish and the calculation unit may be arranged to enter the measurement results in the algorithm and automatically calculate this quality property by means of the algorithm and the measurement results.

In a preferred embodiment the apparatus is arranged to register the intensity of reflected light in the visible and near-infrared range between 400 and 1100 nm. It may be arranged to register the intensity of reflected light both in the visible range, preferably between 400 and 600 nm, and in the near-infrared range, preferably between 850 and 1050 nm.

The apparatus according to the invention may be arranged to register the intensity of reflected light in wavelength bands centred on one or more the following wavelengths: 400 422, 440, 472, 500, 546, 578, 600, 688, 814, 920, 978 nm. At these wavelengths there is a particularly clear correlation between the intensity of reflected light and significant quality properties such as colour, fat content and astaxanthin content.

When the light emitter has a broad spectrum, the light receiver will preferably comprise a spectrophotometer, able to measure the light intensity in the different wavelength bands. This may be a conventional spectrophotometer, which by means of prism or grating divides the light into a spectrum, thus permitting individual or preferred wavelength ranges to be examined by one or more light-sensitive detectors in order to give a measurement for light intensity in different wavelength bands.

In another embodiment of the apparatus the light receiver comprises at least one detector and more than three filters, permitting light in specified wavelength bands in the visible and near-infrared range to pass through, the filters being placed in the optical paths between the light emitter and the detectors. This could be described as a spectrophotometer in a less conventional sense, where different filters are interposed in the light path between the meat and the detector(s). This may provide a more robust design for the photometer. Alternatively the filters may be interposed in the light path between a wide-spectrum light emitter and the meat.

The calculation unit will advantageously comprise an algorithm for determining at least one of the following quality properties: colour, astaxanthin content and fat content, since these properties are of particular interest.

The calculation unit may comprise an algorithm which assigns individual fish a quality class corresponding to the quality property, thus allowing the fish to be sorted or processed according to category.

The device may with particular advantage be arranged at a conveyor for individual transport of the fish to measure the fish singly during transport, in particular freshly slaughtered fish with intact peritoneum. The apparatus according to the invention therefore preferably comprises a conveyor for individual transport of abdominal opened fish with intact peritoneum and scales, and a measurement system for on-line measurement of the fish conveyed.

The calculation unit may comprise an algorithm for detecting faulty areas, the algorithm being arranged to disregard measurement results which deviate significantly from other measurement results from the same or other fish. Only the non-deviating measurement results are used for determining the quality property.

In particular it is preferred that the apparatus according to the invention is designed to perform on-line determination of quality properties of fish on a slaughter line or in a fish grading machine, whereby a conveyor individually conveys fish with cut opened abdomen into, through and out of the reflection measurement device which is placed on the slaughter line or in the grading machine.

Preferably, a non-image-forming light receiver is used, as this allows light to be registered in many wavelength bands, thus giving higher certainty in determining the quality property. For example, a spectrophotometer may be used. The light receiver will preferably be able to register light in bandwidths from 2 to 100 nm. The light receiver may be arranged to receive and register reflected light in 6 to 30, or preferably 8 to 20 different wavelength bands in the visible and near-infrared range. This total of "channels" is sufficient for precise determination of the quality property.

In the present invention, the term fish shall particularly be understood as salmon, but may also be applied to trout, tuna and other fish with high quality requirements.

The invention is described in greater detail in the following with reference to the drawings, in which.

EXAMPLE 1

Design and Function of On-line Measuring Apparatus

A slaughter line for fully automatic slaughtering of salmon comprises a conveyor for individual transport of fishes and tools for processing the fishes after sticking and bleeding.

Figure 1:
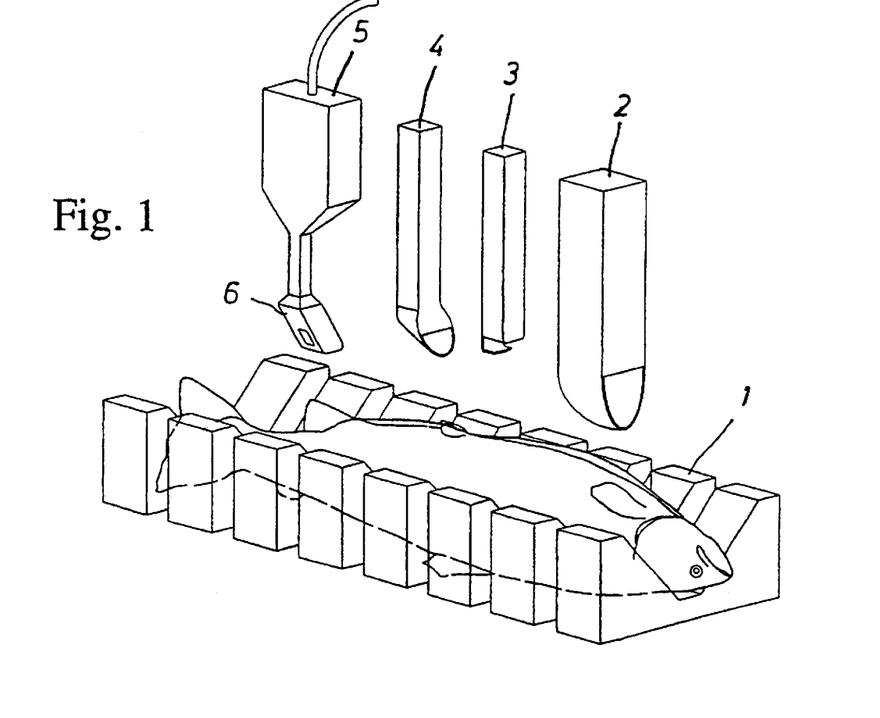
FIG. 1 shows part of a slaughter line with tools for cutting the salmon in the abdomen and removing the viscera together with a measuring unit used in an embodiment of an apparatus according to the invention for illuminating the salmon's inner abdominal wall and measuring the spectrum of light reflected from the abdominal wall.
Figure 2:
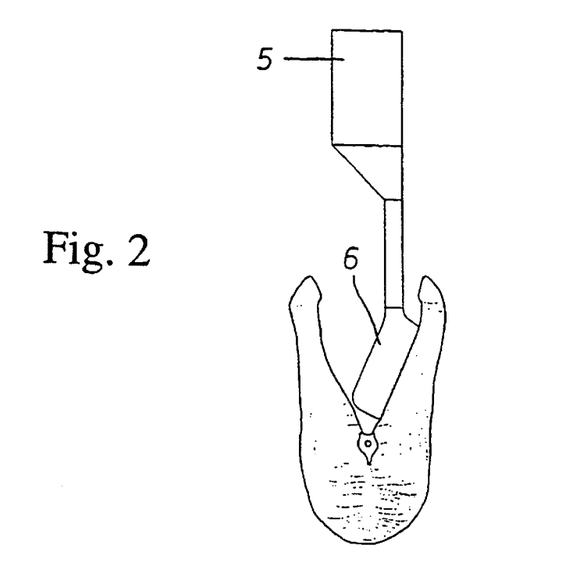
FIG. 2 shows the location of the measuring unit during measurement.

The section of a slaughter line shown in FIG. 1 has a fixture 1 for holding the salmon during transport and tools 2, 3, 4 for eviscerating the salmon after the abdomen has been cut open. A measuring unit 5 with a measuring head 6 is so arranged in a suspension device that it can be moved from the non-active position shown to a measurement position with the measuring head in contact with the inside of the abdomen, as shown in FIG. 2. Positioning is effected by means of, for instance, an air cylinder, which may be controlled by a light relay or a proximity detector which activates the cylinder when the tail fin or similar part of a fish is near the detector.

The measuring unit contains a light emitter which emits light in the visible and near-infrared range from 400 to 1100 nm, e.g. a halogen lamp. The measuring head has a window in the side lying against the inside of the fish. Next to the window is a system arranged to register the intensity of the light reflected from the abdomen in various wavelength bands. Optical fibres may conduct the light of the light emitter to the window and other optical fibres conduct the reflected light from the window to the system arranged to register the intensity, e.g. a spectrophotometer. The system may comprise a grating or prism which disperses the light into a spectrum. A number of light detectors lying behind capture the light in their respective spectral wavelength band. There may e.g. be a row of silicon-type photodiodes or phototransistors.

The measuring unit is connected to a computer unit which receives the signals from the detectors and processes their information. The computer unit also controls the initialisation of start, stop and repeat of a measuring sequence. It further contains a program, which by means of an algorithm is able to interpret the reflection data received and to convert them into a measure of colour, fat content and possibly astaxanthin content. The algorithm may include the weight of the salmon and the weight may be read via a cable or a network connected to a weighing unit.

After the abdomen has been cut, the salmon is moved towards tools 2, 3 and 4, which are automatically lowered to the level of the fish and eviscerate it. Immediately after the tools is the measuring unit 5 which is moved down into the open clean fish so that the measuring head assumes the position shown in FIG. 2, with the head in contact with the peritoneum.

The computer unit now commences a series of measurement sequences so as to record reflection spectra from the inside of the abdomen along the length of the fish while it continues to be transported by the conveyor fixture.

The spectra are stored in the computer and investigated for significant deviations. Any deviating data are disregarded and the remainder are used to form an average spectrum. The intensity values at different wavelength bands of this spectrum are entered into a algorithm in the program, which algorithm are able to interpret the values to a measure of colour, fat content and possibly astaxanthin. The results can be used directly for (automatic) sorting of salmon according to their quality class, or can be used subsequently for controlling/adjusting salmon production in ponds or in connection with dispatch to customers with an interest in salmon with specific quality characteristics, or for the further treatment of salmon at the processing factory, e.g. for identifying the salmon best suited for smoking or filleting.

The device is able to determine the quality of, for instance, over 16 salmon per minute. At extremely high slaughtering or processing rates it may be necessary to measure only a selection of the fish. This may be sufficient where the measurements are primarily intended for monitoring farmed salmon production.

Alternatively, at extremely high slaughtering or processing rates a measuring unit may be used with a measuring head containing several detectors arranged, for instance, in a row along the lengthways direction of the fish. In this way it is possible to measure many part areas of the abdomen in a very short time, as the salmon do not need to be moved between each measurement of a new part-area.

During the actual measurement sequence, the measurement head and fish may be stationary in relation to each other, but preferably a measuring sequence is carried out while the head is stationary and the fish move past at normal conveyor speed.

The apparatus described above for measuring quality properties on a slaughter line can according to a second embodiment be mounted at the conveyor of grading machines known per se which grades freshly slaughtered fish (with open abdomen and intact peritoneum) in different weight classes. The measurement results of the apparatus can be transmitted to the sorting computer of the machine, so that fish may now be sorted on basis of their weight as well as according to other quality properties which are determined by means of the apparatus, or if desired, only on basis of quality properties measured with the apparatus. The method has the advantage of being fast and non-destructive. Current grading machines can process 60 fish per minute.

EXAMPLE 2

Hand-held Apparatus

Figure 3A:
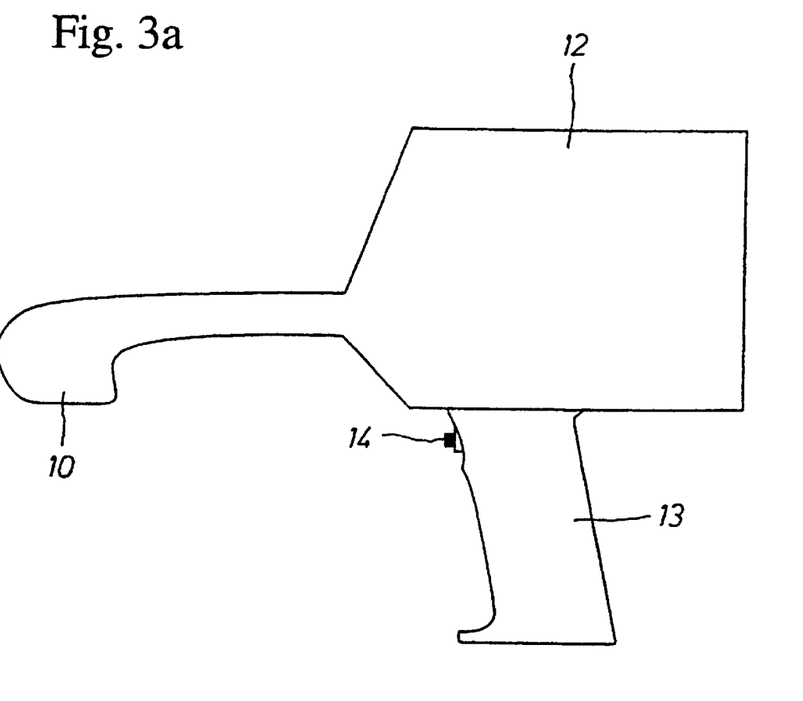
FIGS. 3a and 3b show an embodiment of a hand-held apparatus according to the invention, seen from different angles.
Figure 3B:
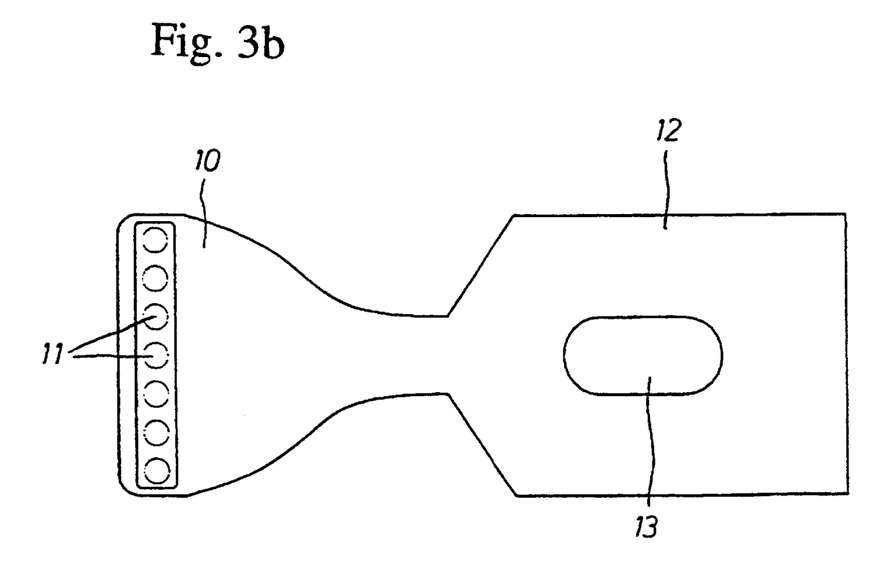

The apparatus in FIGS. 3a and 3b for measuring quality properties of salmon etc. comprises a measuring head 10 with seven measuring windows 11, through which reflection measuring means are able to measure the reflection of a fish part placed opposite the windows, e.g. the inner abdomen of an eviscerated fish. Behind each window is the end of a bundle of optical fibres. The fibre bundles are led into a housing 12 fitted with a handle 13.

In the housing each bundle is divided into two bundles, one of which is connected with a light emitter (e.g. a halogen lamp) and the other with a spectrophotometer, able to register the spectrum of light reflected from the fish.

The housing contains a computer for storing and processing the registered spectra. The computer is also able to compare the measurement results from the seven spectra against each other or against a predetermined standard and to eliminate unsuitable spectra. On the basis of the suitable spectra, the computer calculates the quality properties of the fish, such as colour class and fat percentage, using a stored algorithm. The computer is able to save the results in a memory for subsequent reading in to another computer unit and the apparatus can also have a display showing the result (colour class and fat percentage).

When a fish is to be measured, an operator places the measuring head on, for instance, the inner abdomen of the fish so that as far as possible all windows are in contact with the peritoneum. By pressing a button 14, the operator activates the computer into performing a measuring sequence. The whole measuring procedure, the removal of unsuitable results and the calculation and display of the result are thereafter automatically controlled by the computer. The result may be available within one second.

This hand-held apparatus is particularly fitted for checking purposes and random sampling, as there can be no expectation of the same operating speed as with a fully automated apparatus. However, the apparatus may be used in locations other than a slaughter line, such as ponds for following the development of salmon, or in plants or plant areas processing the cleaned fish into, for instance, fillets or producing smoked salmon.

In a simplified embodiment the apparatus are provided with only one window.

EXAMPLE 3

Determination of Colour, Fat and Astaxanthin in Salmon by Spectroscopy

Over four days 240 salmon are selected in a processing factory. The salmon are removed from the slaughter line immediately before weighing. To obtain the maximum colour variation the salmon are selected as follows: approx. ¼ sexually mature (to obtain light-coloured salmon), and the rest divided between small, medium and large size.

A "Norwegian Cut" is taken from the salmon and sent to a laboratory for traditional analysis of colour (visual colour appraisal according to the Salmofan scale), fat percentage (chemical analysis) and astaxanthin content (chemical analysis).

From the side of the salmon a square sample of 5×10×1 cm with intact peritoneum (but without scale layer) is also taken. These pieces are placed in a plastic holder and measured in a spectrophotometer of type FOSS NIR Systems Model 6500-II.

Figure 8:
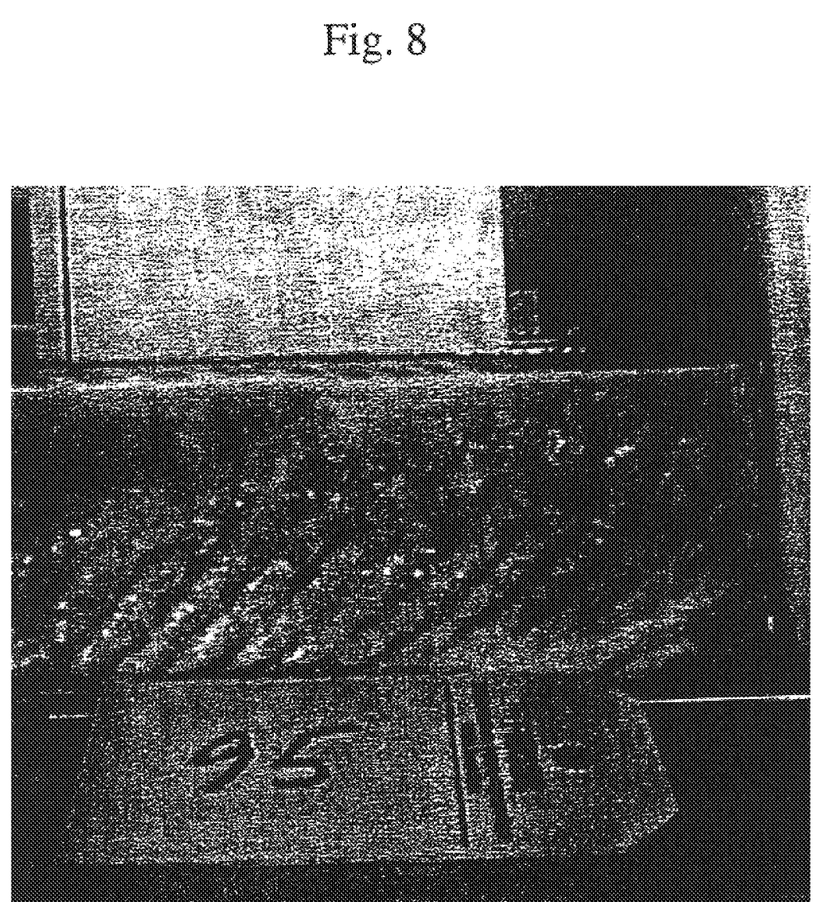
FIG. 8 shows a photo of a salmon's inner abdomen with peritoneum.

FIG. 8 shows a photo of a sample from the inner abdominal side, i.e. the peritoneum side. In one corner the peritoneum is pulled away to reveal the red (dark) meat. Other samples have a peritoneum with more or less opaque areas which can form stripes or islets and obscure the colour of the meat for an observer.

The plastic holder is placed in a transport tube which moves the sample past the instrument's measuring head. The resulting spectrum is an average of 16 measurements taken in a strip approx. 10 mm wide and approx. 100 mm long in the lengthways direction of the sample. The measurement thereby simulates the embodiment of the method according to the invention in which a direct measurement is taken of the opened salmon from the abdominal inner side while the fish is being transported on the slaughter line.

Figure 4:
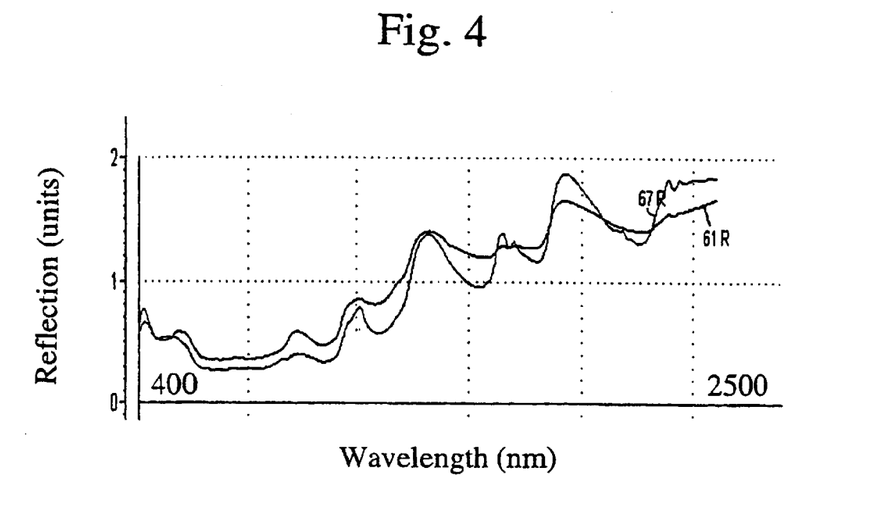
FIG. 4 shows reflection spectra from two salmon with different fat contents.

The reflection spectra cover the spectral range from 400 to 2500 nm. Two examples of reflection spectra are shown in FIG. 4 (61R contains 7.5% fat and 67R 20.3% fat).

The correlation between the spectra and the laboratory values for colour, fat content and astaxanthin content are found by PLS regression analysis. The resulting algorithms are programmed into a calculation unit so that it can calculate colour, fat content and astaxanthin content on the basis of a reflection spectrum.

Among the 240 samples, an "outlier" is found by examination of the spectra. The sample proves to have a very prominent dark spot. An examination of the reflection spectrum may thus detect salmon of abnormal appearance.

Colour

Figure 5:
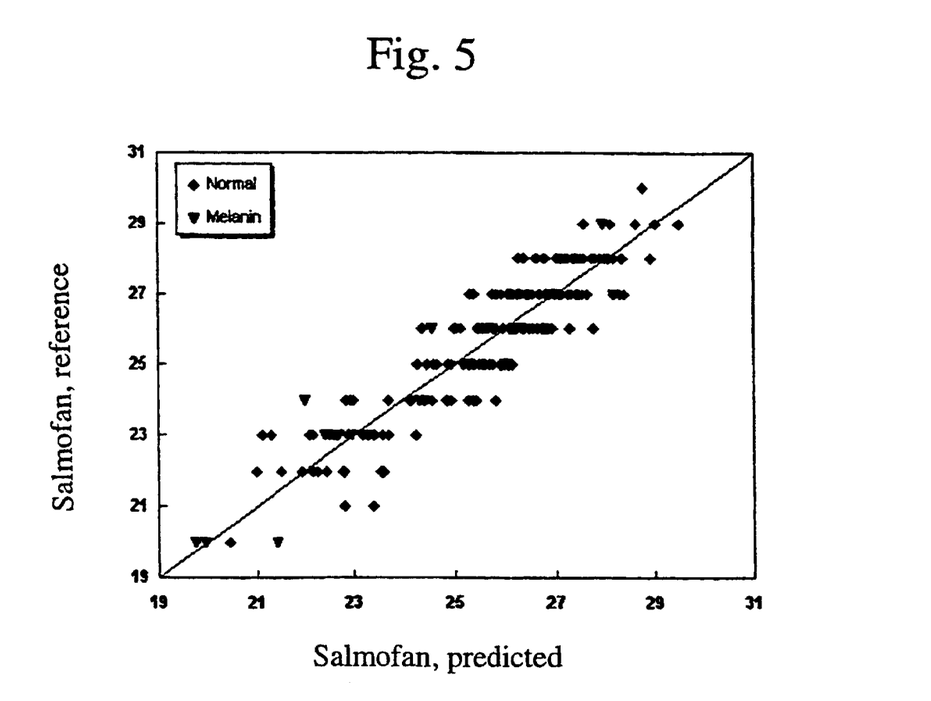
FIG. 5 shows the correlation between subjective colour matching from a colour scale and objective colour measurement from a reflection spectrum.

FIG. 5 shows the correlation between visual colour determination by the Salmofan scale and objective colour determination by analysis of the reflection spectrum. The correlation R between the subjective and objective determinations is 0.914 (standard error prediction, SEP=0.795 units).

If the samples are divided into three colour classes on the basis of the Salmofan scale, 82% are correctly graded by spectral analysis.

On the Salmofan scale, only 7% of the samples differ by two steps, while 93% are in agreement or differ by one step.

Colour determination is possible on all measured salmon by analysis of light reflection.

Fat Content

Figure 6:
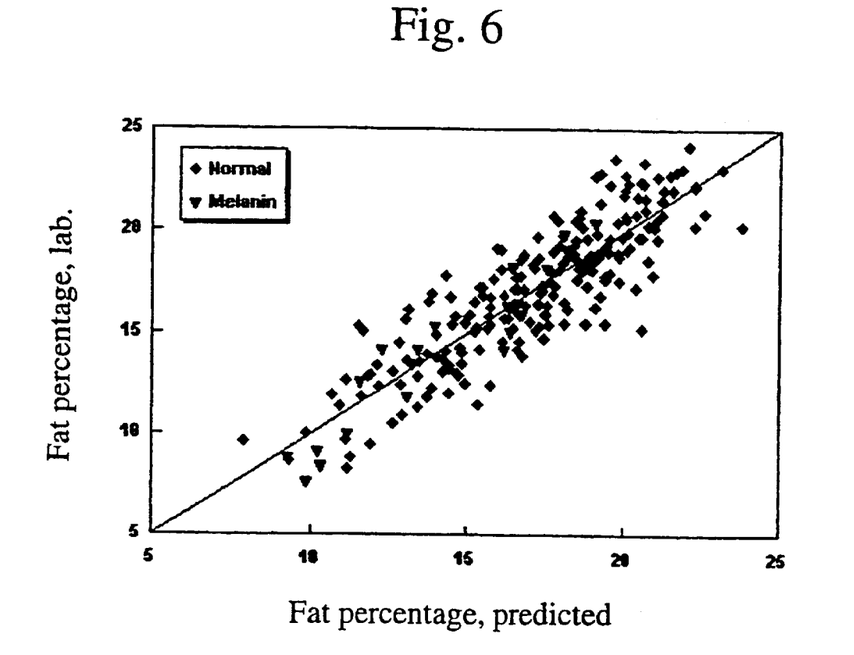
FIG. 6 shows the correlation between fat content in salmon determined by chemical analysis and on the basis of a reflection spectrum.

FIG. 6 shows the correlation between the fat content of salmon meat as determined analytically and by spectral examination. In spectral analysis only that part of the spectrum lying between 400 and 1100 nm is used, as the longer wave spectral range does not contribute positively to determination. When only the spectral range from 400 to 1100 nm is used, a cheap silicon-based detector system in the apparatus is sufficient for on-line measurement of salmon.

20 samples have significant melanin discolouration on the membrane, but this does not affect the spectral determination of fat content. This may be due to the fact that the light in the short wave sector of the spectrum penetrates farther into the sample and is thus unaffected by the nature of the surface. The correlation R between the analytically determined fat content and the content determined by cross-validation of spectra is 0.879 (SEP=1.67%).

Astaxanthin Content

Figure 7:
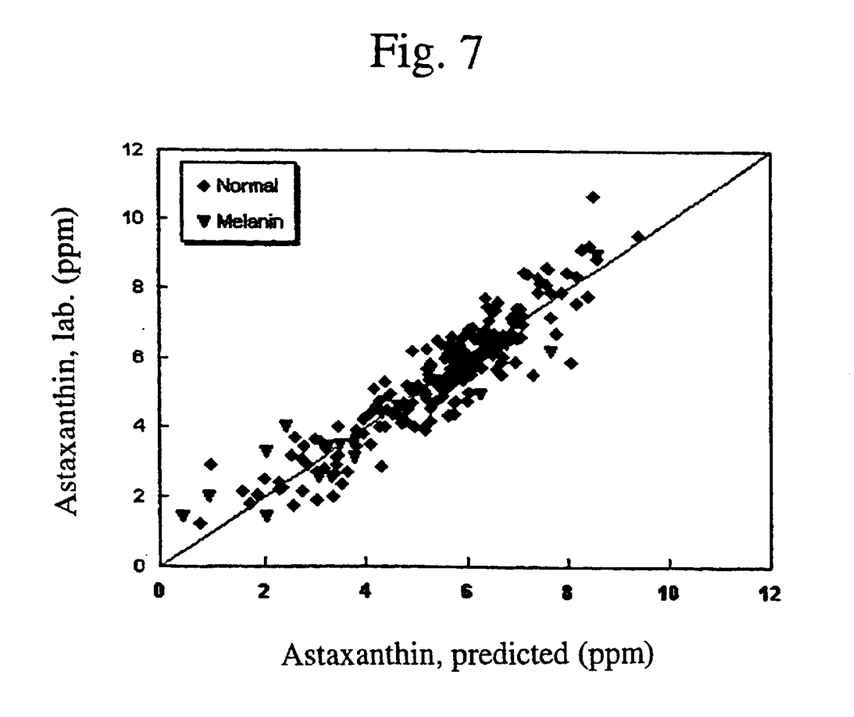
FIG. 7 shows the correlation between astaxanthin contents in salmon determined by chemical analysis and on the basis of a reflection spectrum.

FIG. 7 shows the correlation between analytically determined and spectrally determined astaxanthin content. The correlation R is 0.924 (SEP=0.663). Only reflection data from the wavelength range 400 to 1100 nm are used. The presence of melanin spots has no effect on the determination.

Conclusion

The tests show that spectral measurement with light reflection from the abdominal inner side of slaughtered salmon can be used for rapid determination of colour, fat and astaxanthin with good accuracy. The measurement makes it possible to sort salmon immediately after slaughtering into different classes, depending on colour, fat content and/or astaxanthin content. The method is robust. Even with salmon with significant irregularities in the form of melanin spots, fat accumulations and slaughter errors, reliable measurement results can be obtained. The method measures the salmon through the peritoneum and this has the important advantage that it can already be used after the salmon has been cut open in the abdomen and eviscerated, without the removal of or damage to the peritoneum (nondestructive measurement). The salmon can be measured while in motion. In other words the method can be used directly on the slaughter line or in a subsequent weight grading machine before the cleaned salmon are sent to the buyer for further processing or are further processed at the factory, for instance by smoking.

The tests show that it is sufficient to used near-infrared wavelengths in the short-wave range, which makes the construction of the detector system in the measuring instrument that much cheaper.

What is claimed is:

1. A method for determining quality properties of fish on the basis of light reflection, said method comprising:

A. positioning a fish and a reflection measurement device (5) with a light emitter and a light receiver (6) in relation to each other with the light emitter and light receiver directed towards an inner abdominal wall having peritoneum of the fish, so that the light emitter illuminates an area of the fish through the peritoneum and the light receiver captures the light reflected from the fish;

B. registering the intensity of the reflected light in three or more different wavelength bands in the visible and near-infrared range as measurement results; and C. entering the measurement results registered into an algorithm in a calculation unit, which algorithm expresses a quality property of fish on the basis of the light reflection from the inner abdominal wall with peritoneum, after which the calculation unit automatically calculates the quality property by means of the algorithm and the measurement results.

2. The method according to claim 1, further comprising moving the fish and the light emitter and light receiver (6) of the device in relation to each other in the lengthways direction of the fish during registration of measurement results.

3. The method according to claim 2, further comprising the utilization of a reflection measurement device (5) wherein the light receiver is designed to receive light reflected from an area of the fish with a cross dimension of between at least 5 mm and at most 25 mm and that the reflection measurement device (5) and the fish are moved in relation to each other so that the measurement results are obtained from areas which together form a stripe in the lengthways direction of the fish, the length dimension of the stripe being between 2.5 to 25 longer than said cross dimension.

4. The method according to claim 1, further comprising registering measurement data for different areas of the fish and that at least one set of measurement data is used to express the quality property of the fish.

5. The method according to claim 1, further comprising repeating the registration several times, wherein the fish and the light emitter and light receiver (6) are moved in relation to each other between two measurement sequences, and that at least one set of data resulting from the registrations is entered into the algorithm.

6. The method according to claim 1, further comprising cutting open and eviscerating the fish abdomen before a measurement head of the reflection measurement device and the fish are positioned in relation to each other, by positioning the measurement head in contact with the peritoneum of the inner abdominal wall of the fish.

7. The method according to claim 1, further comprising registering the intensity of reflected light in the visible and near-infrared range between 400 and 1100 nm.

8. The method according to claim 1, further comprising registering the intensity of reflected light both in the visible range, between 400 and 600 nm, and in the near-infrared range, between 850 and 1050 nm.

9. The method according to claim 1, further comprising utilizing the light emitter to illuminate an area of the fish with broad-spectrum light in the visible and near-infrared range.

10. The method according to claim 1, further comprising communicating the measurement results into an algorithm expressing a second quality property of fish, after which the calculation unit calculates the second quality property of the fish.

11. The method according to claim 1, further comprising determining the quality properties on a slaughter line for fish conveyed into, through, and out of said reflection measurement device (5) as mounted on the slaughter line.

12. The method according to claim 1, further comprising determining the quality properties in a fish-grading machine for fish conveyed into, through, and out of said reflection measurement device as mounted in said fish-grading machine.

13. An apparatus for determining quality properties of fish on the basis of light reflection, comprising:
   A. a reflection measurement device (5) having a light emitter and a light receiver (6) and positioners constructed and arranged for placing the reflection measurement device and the fish in relation to each other, the light emitter and light receiver (6) being directed towards an inner abdominal wall having peritoneum of the fish, light emitter illuminating an area of the fish through the peritoneum and the light receiver capturing light reflected from the fish;
   B. a registration unit connected to the light receiver of the reflection measurement device (5), the registration unit registering the intensity of reflected light in three or more different wavelength bands in the visible and near-infrared range, providing measurement results; and
   C. a calculation unit having an algorithm expressing a quality property of the fish from the light reflection of the inner abdominal wall with peritoneum, the calculation unit receiving said registered intensities of reflected light for communication into the algorithm for processing to calculate the quality property of said fish.

14. The apparatus according to claim 13, further comprising a conveyor arranged to move the fish and the light emitter and light receiver (6) in the lengthways direction of the fish during registration of the measurement results.

15. The apparatus according to claim 13, wherein the registration unit registers the intensity of reflected light in different areas of the fish.

16. The apparatus according to claim 13, further comprising a repeating cycle constructed to repeat the registration of the intensity of reflected light, and a conveyor arranged to move the fish and the light emitter and light receiver (6) between two measuring sequences.

17. The apparatus according to claim 13, wherein the light emitter emits broad-spectrum light in the visible and near-infrared range.

18. The apparatus according to claim 13, wherein the calculation unit calculates a second quality property of fish, the calculation unit being arranged to enter the measurement results of said second quality property into the algorithm, said algorithm calculating said second quality property of said fish.

19. The apparatus according to claim 13, wherein registration of the intensity of reflected light occurs in the visible and near-infrared range between 400 and 1100 nm.

20. The apparatus according to claim 13, wherein registration of the intensity of reflected light occurs both in the visible range, between 400 and 600 nm, and in the near-infrared range, between 850 and 1050 nm.

21. The apparatus according to claim 13, wherein the wavelength of the reflected light is selected from the group consisting of: 400 nm, 422 nm, 440 nm, 472 nm, 500 nm, 546 nm, 578 nm, 600 nm, 688 nm, 814 nm, 920 nm, and 978 nm.

22. The apparatus according to claim 13, the light receiver comprising a spectrophotometer.

23. The apparatus according to claim 13, the light receiver comprising at least one detector and at least three filters, said filters being positioned in optical paths between the light emitter and the detectors permitting light transmission in specified wavelength bands in the visible and near-infrared range.

24. The apparatus according to claim 13, the calculation unit comprising an algorithm for determining at least one of the following group of quality properties consisting of color, Astaxanthin content, and fat content.

25. The apparatus according to claim 13, the calculation unit comprising an algorithm which assigns to individual fish a quality class corresponding to the quality property.

26. The apparatus according to claim 13, further comprising a conveyor constructed to transport abdominally opened fish with intact peritoneum, and a reflection measurement device (5) for on-line measurement of the fish.

27. The apparatus according to claim 13, the calculation unit comprising an algorithm for detecting faulty measurement results, the algorithm being arranged to disregard measurement results which deviate significantly from other measurement results of said fish.

28. The apparatus according to claim 13, further comprising a conveyor for transporting fish having a cut abdomen into, through, and out of the reflection measurement device, said reflection measurement device being placed on a slaughter line, said reflection measurement device measuring quality properties of said fish on said slaughter line.

29. The apparatus according to claim 13, further comprising a conveyor for transporting fish having a cut abdomen into, through, and out of the reflection measurement device, said reflection measurement device being placed in a fish-grading machine, said reflection measurement device measuring quality properties of said fish in said fish-grading machine.

\* \* \* \* \*